United States Patent

Kondo et al.

[11] Patent Number: 5,491,248
[45] Date of Patent: Feb. 13, 1996

[54] READILY DISPERSIBLE BENTONITE

[75] Inventors: Mitsuji Kondo, Kuroiso; Takeo Sawada, Takasaki, both of Japan

[73] Assignee: Hojun Kogyo Co., Ltd., Annaka, Japan

[21] Appl. No.: 425,534

[22] Filed: Apr. 20, 1995

[30] Foreign Application Priority Data

Feb. 1, 1995 [JP] Japan .................................. 7-34692

[51] Int. Cl.$^6$ ........................................... C07F 5/06
[52] U.S. Cl. ............................... 556/173; 507/127
[58] Field of Search ............................ 556/176; 507/127

[56] References Cited

U.S. PATENT DOCUMENTS

| | | | |
|---|---|---|---|
| 4,528,038 | 7/1985 | Williams | 556/173 X |
| 5,110,501 | 5/1992 | Knudson et al. | 556/173 X |
| 5,292,908 | 3/1994 | Onikata et al. | 556/173 |

*Primary Examiner*—Paul F. Shaver
*Attorney, Agent, or Firm*—Kenyon & Kenyon

[57] ABSTRACT

Readily dispersible bentonite comprising bentonite particles having adsorbed an alkyl-substituted silane compound represented by formula (I) onto the surface thereof is disclosed:

$$R_a SiX_b \quad (I)$$

wherein R represents an alkyl group having 1 to 18 carbon atoms; X represents a methoxy group, an ethoxy group or a halogen atom; a and b each represents 1, 2 or 3, provided that (a+b) is 4; in an amount of not more than 1% by weight based on the bentonite. When poured into water and stirred, the treated bentonite is rapidly dispersed while minimizing formation of hardly dispersible lumps of powder to provide an aqueous bentonite dispersion exhibiting satisfactory viscosity and water impermeability.

2 Claims, No Drawings

READILY DISPERSIBLE BENTONITE

FIELD OF THE INVENTION

This invention relates to readily dispersible bentonite which can rapidly be dispersed in water while retaining viscosity and water impermeability inherent to bentonite.

BACKGROUND OF THE INVENTION

Bentonite is supplied on the market in a powdered form having a particle size of not greater than 150 μm, which is prepared by coarsely crushing ore from a bentonite mine, which contains about 10 to 40 wt % of water, to a size of about 10 mm or less, drying it in a rotary drier to reduce the water content to about 6 to 10 wt %, and pulverizing it in a roller mill or a hammer mill to the above size.

A soil stabilizing fluid used in civil engineering works, such as underground continuous wall construction or in-situ piling, and a drilling fluid (mud) used in development of underground resource energy, for example, drilling of an oil well, a geothermal well or a spring well, is generally prepared by dispersing powdered bentonite in fresh water in a concentration of 4 to 8 wt % by stirring it in a stirring machine and, if desired, adding adequate amounts of chemical substances, such as sodium carboxymethyl cellulose, polymers and surface active agents, in order to prevent deterioration due to contamination with cement or a brine such as seawater. On being poured into water, powdered bentonite first forms lumps, which are then disintegrated by stirring it a long time into a uniform dispersion. In what follows, the single term "lumps" means undissolved lumps of powder which are formed when the powder is poured into water. Therefore, preparation of a soil stabilizing slurry or mud has required great energy and time for stirring. The higher the viscosity and water impermeability of bentonite due to the higher bonding force with water, that is, the higher the quality of bentonite, the greater the tendency to formation of lumps of powder which are hard to disperse in water.

As the depth reached by recent ground drilling works has increased, the demand for a stabilizing slurry or mud having high water impermeability sufficient to withstand high underground water pressure has been increasing. While bentonite of high quality meeting that demand has been supplied, bentonite satisfying the requirements for easy dispersion as well as high quality has been keenly sought.

Efforts have hitherto been made to satisfy the above requirements. For example, a grinding method for minimizing formation of fine particles of 75 μm or smaller which are apt to form lumps was suggested. Removal of fine particles by air classification was also attempted. However, all the conventional attempts failed to achieve satisfactory results.

Bentonite is an alkaline clay mainly comprising a clay mineral montmorillonite and, unlike other clay minerals such as kaolinite or pyrophyllite, has a great cation-exchange capacity of 40 to 120 milliequivalents per 100 g of clay. The exchangeable cations include a sodium ion, a calcium ion, and a magnesium ion. In particular, bentonite having an abundance of sodium ions has such high hydrophilic properties that it absorbs a large quantity of water to increase its own volume remarkably, that is, it exhibits high swellability in water and is finally dispersed to colloidal particles and therefore has been used as a fundamental element of a stabilizing slurry or mud for drilling or boring works. Essential functions required for the material of stabilizing slurries or mud are proper viscosity and water impermeability.

SUMMARY OF THE INVENTION

Accordingly, an object of the present invention is to provide readily dispersible bentonite which can be rapidly dispersed in water while minimizing formation of lumps without substantial reduction in viscosity and water impermeability inherent to bentonite.

That is, the present invention relates to readily (water) dispersible bentonite obtained by surface treating bentonite by with adding at least one alkyl-substituted silane compound represented by formula (I);

$$R_a SiX_b \qquad (I)$$

wherein R represents an alkyl group having 1 to 18 carbon atoms; X represents a methoxy group, an ethoxy group or a halogen atom; a and b each represents 1, 2 or 3, provided that (a+b) is 4; in an amount of not more than 1% by weight based on the bentonite.

Bentonite powder comprises solid bentonite particles with a water content adsorbed on the surface thereof and air filling the gaps among the particles, and the particles agglomerate to form porous clay particles. The clay particles have a highly hydrophilic and highly polar surface and therefore tend to gather. Thus, when bentonite powder is poured into water, the individual bentonite particles do not come into contact with water but gather to form clusters with a large amount of air entrapped therein, and only the outermost part of the clusters is first to be brought into contact with water. Where the bentonite contains abundant sodium ions, the surface of the bentonite cluster absorbs water owing to its strong hydrophilic properties and immediately smells with water to form a continuous water-impermeable gel film. Since the gel film is water impermeable and also adhesive, the air entrapped in the inside of the cluster cannot easily be displaced with outside water. It follows that the bentonite clusters rise to the water surface as lumps in the initial stage of stirring. If the lumps come into contact with each other in a turbulent flow by stirring, they tend to grow into larger lumps. In this stage, the lumps consist of white powder with its inside remaining dry. In the meantime, displacement of inside air with outside water through the gel film proceeds with time, and the water having entered through the gel film swells inside bentonite particles to gradually increase the transparency. At the same time, the lumps are disintegrated from their outermost part and become thinner. Finally, all lumps disappear to provide a uniform dispersion.

Accordingly, in order to accomplish the object of the present invention, it would be an effective means to temporarily suppress formation of a continuous water-impermeable gel film in the initial stage of stirring, namely, when powdered bentonite is poured into water and comes into contact with water. The inventors of the present invention have found that existence of an adequate amount of a hydrophobic substance on the surface of bentonite particles is desirable for that effect. Such a hydrophobic substance as meets the object should satisfy the following conditions; (1) to have no adverse influence on the viscosity and water impermeability of bentonite, (2) to produce a desired effect upon addition of a small amount, (3) to be moderately priced so that the increase in production cost of bentonite may be within an acceptable range, and (4) to be applied to the surface of bentonite particles by a simple and easy method.

The means established by the present inventors is as follows. Coarsely crushed and dried ore of bentonite obtained by a conventional process for bentonite production is pulverized while sprinkling a proper amount of at least one of the following alkyl-substituted silane compounds, or powdered bentonite is mixed with a proper amount of at least one of the alkyl-substituted silane compounds which is added through sprinkling over the powdered bentonite, the compound thereby adhering as a hydrophobic substance on the surface of bentonite particles.

DETAILED DESCRIPTION OF THE INVENTION

The alkyl-substituted silane compounds which can be used in the present invention are represented by formula (I):

$$R_a SiX_b \tag{I}$$

wherein R represents an alkyl group having 1 to 18 carbon atoms (more preferably 1 to 6 carbon atoms); X represents a methoxy group, an ethoxy group or a halogen atom; a and b each represent 1, 2 or 3; and (a+b) is 4.

Typical examples of the alkyl-substituted silane compounds include methyltrimethoxysilane [$CH_3Si(OCH_3)_3$], trimethylchlorosilane [$(CH_3)_3SiCl$], trimethylmethoxysilane [$(CH_3)_3SiOCH_3$], hexyltrimethoxysilane [$C_6H_{13}Si(OCH_3)_3$], dodecyltriethoxysilane [$(CH_{12}H_{25}Si(OC_2H_5)_3$], and octadecyltriethoxysilane [$C_{18}H_{37}Si(OC_2H_5)_3$].

There is generally an optimum range of the amount of the alkyl-substituted silane compound to be added to bentonite depending on the kind of bentonite and the kind of the alkyl-substituted silane compound. If the amount of the alkyl-substituted silane compound added is lower than the respective optimum range, inhibition of the formation of lumps is insufficient. If the amount exceeds the optimum range, although the formation of lumps is inhibited, the bentonite clusters exhibit water repellency and thereby poor dispersibility. The optimum range for a combination of specific bentonite species and a specific alkyl-substituted silane compound can be decided by preliminary experimentation for evaluating the inhibitory effect on lump formation as well as the viscosity and water impermeability of the resulting dispersion. In many cases, the amount to be added for producing a noticeable effect is from 0 to 1% by weight, preferably from 0.05 to 0.5% by weight, based on bentonite.

The water content of the bentonite to which the alkyl-substituted silane compound is added may be in the same range as that of commonly available bentonite products, i.e., in the range of from about 6 to 10% by weight. There is no need to dry or dehydrate bentonite to a substantially water-free state as has been necessary in a conventional surface treatment of inorganic silicate fillers with a silane coupling agent. Neither is it necessary to limit the water content of bentonite to be treated.

The alkyl-substituted silane compound added to bentonite powder in an amount of not more than 1% by weight renders a part of the surface of bentonite particles hydrophobic owing to its remarkable water-repelling action attributed to the alkylsilyl group thereof. As a result, when the thus treated bentonite is poured into water, the surface of the bentonite particles is moderately prevented from absorbing water to form a continuous water-impermeable gel film. It follows that the clusters of bentonite particles achieve rapid displacement of the internal air with the outside water while minimizing formation and growth of lumps, and the clusters are crumbled and dispersed in water at a considerably increased speed by the turbulent flow of stirring.

The alkyl-substituted silane compound used in the present invention is hydrolyzed on contact with water, thereby releasing the methoxy or ethoxy group by dealcoholization, or halogen atom by dehalogenation and, at the same time, providing a hydroxyl group on the silicon atom (to form a silanol group). Since the resulting silanol group is hydrophilic, it is adhered to the hydrophilic surface of the water-containing bentonite particles.

As a technique relevant to the present invention, U.S. Pat. No. 5,292,908 discloses modified bentonite which is dispersed in water to perform a function of adjusting rheology of an aqueous fluid, which is obtained by adding an alkyl-trialkoxysilane to bentonite in such an amount that the resulting bentonite may not lose the water dispersibility, usually in an amount of 1 to 10 parts by weight per 100 parts by weight of bentonite, followed by treating in a water-free atmosphere to add an alkylsilico group to a part of the surface of bentonite particles. This technique is quite different from the present invention; the modified bentonite of U.S. Pat. No. 5,292,908 has an alkylsilico group permanently added to the surface thereof through a covalent bond that is formed by condensation (dealcoholation) between a hydroxyl group on the edge of montmorillonite crystal grains and the alkyltrialkoxysilane. Therefore, the treatment is accomplished under a water-free condition. On the other hand, in the present invention, the alkyl-substituted silane compound merely has to be physically adhered to the surface of water-containing bentonite particles so that the surface of the bentonite particles may temporarily exhibit hydrophobic properties to prevent formation of lumps immediately after the bentonite particles are poured into water and in the initial stage of stirring. Therefore, the silane compound does not need to be permanently bound to the surface of bentonite particles through a chemical bond, and the amount of the silane compound to be added may be lower than the lower limit required for the above-described modified bentonite. The viscosity and water impermeability inherently possessed by bentonite are substantially guaranteed in the presence of such an alkyl-substituted silane compound.

The present invention will now be illustrated in greater detail with reference to examples and comparative examples, but it should be understood that the present invention is not construed as being limited thereto. Unless otherwise indicated, all the parts and percents are by weight.

EXAMPLE 1

Coarsely crushed and dried bentonite ore from Greybull, Wyo., U.S.A., weighing 25 kg (water content: 9.0%) was uniformly spread on a polyethylene sheet to a thickness of about 10 mm, and 50 g of methyltrimethoxysilane was sprayed over the bentonite. Immediately thereafter, the bentonite ore was gathered at the central portion of the sheet and passed through a hammer mill twice to obtain pulverized powder of treated bentonite (hereinafter designated Treated Bentonite I). For comparison, non-treated bentonite pulverized powders were prepared in the same manner as described above except for using no methyltrimethoxysilane. The particle size distribution of the pulverized powders measured through a dry sieve test is shown in Table 1. As shown in Table 1, both the Treated Bentonite I and the non-treated bentonite had approximately the same particle size distribution.

TABLE 1

Particle Size Distribution

| Sieve Opening (μm) | Non-treated Bentonite (%) | Treated Bentonite I (%) |
| --- | --- | --- |
| 150 or more | 2.4 | 3.9 |
| 150–75 | 20.0 | 15.3 |
| 75–45 | 34.6 | 32.8 |
| 45 or less | 43.0 | 48.0 |

Treated Bentonite I was compared with the non-treated bentonite in inhibitory effect on lump formation as follows.

In a 1 l-beaker was put 600 ml of tap water (conductivity: 133 μS/cm; pH 7.2). Sample bentonite (42 g) was added thereto and immediately thereafter stirred in a DC 6-wing turbine stirrer "Model DS-2R" at 500 rpm for 5 minutes. The stirring was stopped to observe lumps of powder rising to the water surface. The results obtained are shown in Table 2. It is seen that Treated Bentonite I according to the present invention extremely suppresses formation of lumps, and the lumps allow rapid permeation of water.

TABLE 2

| | Non-treated Bentonite | Treated Bentonite I |
| --- | --- | --- |
| Size of lumps (diameter; mm) | 2–5 | 1–2 |
| Number of lumps | 40 | 10 |
| State of lumps (as visually observed) | dry powder remaining in the inside | the inside permeated with water |

After the observation, the stirring was resumed. The lumps of Treated Bentonite I completely disappeared after 10 minutes (in total) of stirring. On the other hand, it took 30 minutes (in total) of stirring for the lumps of the non-treated bentonite to completely disappear. The viscosity and water impermeability of each of the resulting bentonite dispersion are shown in Table 3. The viscosity was measured with a Fan VG rotational viscometer which is in conformity with the specification of the U.S. Petroleum Institute. The water impermeability was evaluated in terms of fluid loss (expressed in amount of filtrate obtained in 30 minutes under pressure of 3 kgf/cm$^2$ and thickness of filter cake) as measured with a constant pressure filtration tester according to the same specification.

TABLE 3

| | Non-treated Bentonite | Treated Bentonite I |
| --- | --- | --- |
| Viscosity: | | |
| Apparent viscosity (cP) | 13.4 | 15.5 |
| Plastic viscosity (cP) | 10.6 | 12.3 |
| Yield value (lb/100 ft$^2$) | 5.6 | 6.4 |
| Gel strength (lb/100 ft$^2$) | | |
| Initial | 1.5 | 1.5 |
| After 10 minutes | 7.5 | 6.5 |
| Water impermeability: | | |
| Fluid loss (ml/30 min, 3 kgf · cm$^{-2}$) | 14.2 | 13.2 |
| Thickness of cake (mm) | 1.8 | 1.6 |

As is apparent from the results of Table 3, Treated Bentonite I was proved equal or even superior to the non-treated bentonite in the viscosity and water impermeability.

EXAMPLE 2

Bentonite was treated with various alkyl-substituted silane compounds shown in Table 4 in the same manner as in Example 1 to prepare Treated Bentonite II to VI. Treated bentonite II to VI were evaluated by a dispersion test in the same manner as in Example 1. The results obtained are shown in Table 4. It is seen that the treated bentonite according to the present invention exhibits excellent dispersibility while retaining viscosity and water impermeability.

TABLE 4

| | Non-treated Bentonite | II | III | IV | V | VI |
| --- | --- | --- | --- | --- | --- | --- |
| Treating agent | none | 0.3% trimethyl-chloro-silane | 0.3% trimethyl-methoxy-silane | 0.2% hexyltri-methoxy-silane | 0.3% dodecyl-triethoxy-silane | 0.3% octadecyl-triethoxy-silane |
| Time required for lumps to disappear (min) | 33 | 15 | 13 | 15 | 13 | 16 |
| Viscosity: | | | | | | |
| Apparent viscosity (cP) | 12.5 | 13.9 | 12.4 | 13.5 | 13.5 | 14.8 |
| Plastic viscosity (cP) | 10.5 | 10.3 | 10.8 | 9.0 | 11.0 | 12.7 |
| Yield value (lb/100 ft$^2$) | 4.0 | 7.2 | 3.2 | 9.0 | 5.0 | 4.1 |
| Gel strength (lb/100 ft$^2$): | | | | | | |
| Initial | 1.5 | 1.5 | 1.5 | 1.0 | 1.5 | 1.0 |
| After 10 minutes | 6.5 | 8.0 | 8.0 | 6.0 | 8.0 | 5.5 |
| Water impermeability: | | | | | | |
| Fluid loss (ml/30 min, 3 kgf · cm$^{-2}$) | 16.3 | 14.1 | 14.8 | 15.8 | 15.2 | 13.5 |
| Thickness of cake (mm) | 2.0 | 1.9 | 2.1 | 2.0 | 2.0 | 1.8 |

EXAMPLE 3

In an Eirich mixer "Model RV02" was charged 3000 g of bentonite "Superclay" (a product of Hojun Yoko K.K., produced by grinding bentonite of Greybull, Wyo., U.S.A., in a roller mill), and a varied amount of methyltrimethoxysilane was added thereto as shown in Table 5, followed by stirring at 900 rpm for 5 minutes. The dispersibility of the resulting treated bentonite was evaluated by observing the state of lumps after 5 minutes of stirring in water in the same manner as in Example 1. The results obtained are shown in Table 5.

TABLE 5

| Sample No. | SC-0 | SC-1 | SC-2 | SC-3 | SC-4 | SC-5 |
|---|---|---|---|---|---|---|
| Composition (part): | | | | | | |
| Superclay | 100 | 100 | 100 | 100 | 100 | 100 |
| Methyltrimethoxysilane | 0 | 0.05 | 0.1 | 0.2 | 0.5 | 1.0 |
| Dispersibility (5 minutes' stirring): | | | | | | |
| Size of lumps (diameter, mm) | 6-3 | 3-2 | 2-1 | 2-1 | 2-1 | 1-0 |
| Number of lumps | 50 or more | 30 | 20 | 20 | 20 | 10 |
| State of lumps | D | D | W | W | W | W |

Note
D: Dry powder remained in the inside of lumps.
W: Wet as a whole (with water permeated to the inside).

As is apparent from the results in Table 5, addition of 0.05% methyltrimethoxysilane (SC-1) appreciably reduces lump formation as compared with the untreated bentonite (SC-0), and lump formation is further suppressed by addition of increased amounts, i.e., 0.1% or more, of methyltrimethoxysilane to exhibit satisfactory water dispersibility.

Performance of samples SC-0, SC-2, and SC-3 as mud was tested in accordance with the bentonite testing method specified by the U.S. Petroleum Institute. The results obtained are shown in Table 6. As is apparent from the results of Table 6, the treated bentonite according to the present invention was satisfactory in viscosity and water impermeability.

TABLE 6

| | SC-0 | | SC-2 | | SC-3 | |
|---|---|---|---|---|---|---|
| | Initial | After 1 Night | Initial | After 1 Night | Initial | After 1 Night |
| Apparent Viscosity (cP) | 20.0 | 21.6 | 19.2 | 21.2 | 19.8 | 21.6 |
| Plastic viscosity (cP) | 15.1 | 16.3 | 14.2 | 16.3 | 15.1 | 16.2 |
| Yield value (lb/100 ft²) | 9.7 | 10.5 | 10.0 | 9.8 | 9.3 | 10.8 |
| Gel strength (lb/100 ft²) | | | | | | |
| Initial | 1.5 | 1.0 | 1.5 | 1.5 | 1.0 | 1.0 |
| After 10 minutes | 4.0 | 4.5 | 5.0 | 7.0 | 6.0 | 7.0 |
| Fluid loss (ml/30 min, 3 kgf · cm⁻²) | 12.0 | 11.4 | 12.0 | 11.3 | 11.9 | 11.2 |

TABLE 6-continued

| | SC-0 | | SC-2 | | SC-3 | |
|---|---|---|---|---|---|---|
| | Initial | After 1 Night | Initial | After 1 Night | Initial | After 1 Night |
| Thickness of cake (mm) | 2.0 | 1.9 | 2.2 | 2.0 | 2.2 | 2.1 |

As having been fully described and demonstrated, the present invention brings about the following effects.

When the bentonite particles having adhered on the surface thereof an alkyl-substituted silane compound are poured into water and stirred in the preparation of an aqueous bentonite dispersion, the strong water repellency of the alkylsilyl group prevents clusters of the bentonite particles from absorbing water at the outermost part thereof and from forming a continuous water impermeable gel film there in the initial stage of stirring. As a result, formation and growth of lumps of powder are suppressed and, at the same time, displacement of air entrapped inside the cluster with the outside water rapidly proceeds, whereby the whole cluster is swollen with water. The small lumps of powder having lost buoyancy are sufficiently moved in water by a stirring turbulent flow and rapidly become thinner and uniformly dispersed. The readily dispersible bentonite according to the present invention retains the viscosity and water impermeability essential to bentonite and therefore makes it possible to remarkably reduce the time and energy for dispersing bentonite in the preparation of a soil stabilizing slurry or mud for use in ground drilling works.

While the invention has been described in detail and with reference to specific examples thereof, it will be apparent to one skilled in the art that various changes and modifications can be made therein without departing from the spirit and scope thereof.

What is claimed is:

1. Readily dispersible bentonite obtained by surface-treating bentonite with at least one alkyl-substituted silane compound represented by formula (I):

$$R_a SiX_b \tag{I}$$

wherein R represents an alkyl group having 1 to 18 carbon atoms; X represents a methoxy group, an ethoxy group or a halogen atom; a and b each represents 1, 2 or 3, provided that (a+b) is 4;
in an amount of not more than 1% by weight based on the bentonite.

2. Readily dispersible bentonite as claimed in claim 1, wherein said alkyl-substituted silane compound is selected from the group consisting of methyltrimethoxysilane, trimethylchlorosilane, trimethylmethoxysilane, hexyltrimethoxysilane, dodecyltriethoxysilane, and octadecyltriethoxysilane.

* * * * *

UNITED STATES PATENT AND TRADEMARK OFFICE
CERTIFICATE OF CORRECTION

PATENT NO. : 5,491,248
DATED : February 13, 1996
INVENTOR(S) : Mitsuji Kondo, et. al.

It is certified that error appears in the above-indentified patent and that said Letters Patent is hereby corrected as shown below:

Column 2, line 13, delete "with"--.

Signed and Sealed this

Fourth Day of June, 1996

Attest:

BRUCE LEHMAN

*Attesting Officer*  *Commissioner of Patents and Trademarks*